United States Patent [19]

Ward

[11] Patent Number: 4,954,333

[45] Date of Patent: Sep. 4, 1990

[54] TRANSPARENT ANTIPERSPIRANT COMPOSITIONS AND METHOD OF PREPARATION

[75] Inventor: Andrew H. Ward, Midland County, Mich.

[73] Assignee: Dow Corning Corporation, Midland, Mich.

[21] Appl. No.: 304,075

[22] Filed: Jan. 31, 1989

[51] Int. Cl.$^5$ .................. A61K 7/32; A61K 7/34; A61K 7/36; A61K 7/38

[52] U.S. Cl. .................. 424/66; 424/DIG. 5; 424/67; 424/68; 556/9; 556/10; 556/12; 556/173

[58] Field of Search ............... 424/66, 68, 67, DIG. 5; 556/10, 9, 12, 173

[56] References Cited

U.S. PATENT DOCUMENTS

| | | | |
|---|---|---|---|
| 3,184,418 | 5/1965 | Woods et al. | 556/173 |
| 3,373,178 | 3/1968 | Schmidt et al. | 556/12 |
| 4,346,079 | 8/1982 | Roehl | 424/65 |
| 4,434,103 | 2/1984 | Interrante | 556/173 |
| 4,474,704 | 10/1984 | Sawicki | 556/10 |
| 4,528,038 | 7/1985 | Williams | 556/173 |
| 4,605,554 | 8/1986 | Prussin et al. | 424/68 |
| 4,645,847 | 2/1987 | Panster et al. | 556/10 |
| 4,704,271 | 11/1987 | Hourihan et al. | 424/DIG. 5 |
| 4,725,430 | 2/1988 | Schamper et al. | 424/DIG. 5 |

Primary Examiner—Dale R. Ore
Attorney, Agent, or Firm—Marc C. Pawl; Sharon K. Severance

[57] ABSTRACT

The invention relates to compositions for transparent or translucent antiperspirants comprising a polyol, the reaction product of an antiperspirant salt and a silane and an optional gelling agent, but no or substantially no water. When gelled, the composition is suitable for use as a stick antiperspirant. The invention also relates to the process by which compositions of the invention are prepared.

9 Claims, No Drawings

TRANSPARENT ANTIPERSPIRANT COMPOSITIONS AND METHOD OF PREPARATION

BACKGROUND OF THE INVENTION

This application relates to compositions of matter which contain antiperspirant salt materials, wherein the compositions are transparent or translucent in appearance, are relatively free of water and are optionally moldable or otherwise shapeable so as to form antiperspirant sticks.

It is widely known in the industry that consumers place a high value on personal care materials which are clear or transparent. The perceived value is at least partially attributable to the aesthetic appearance of such materials and also the association in the mind of the consumer of transparency with purity of the product. As a consequence thereof, it is deemed very desirable in the personal care industry to formulate transparent or highly translucent antiperspirant compositions, especially those which can be formed into antiperspirant stick configurations. Forms of transparent antiperspirant salt containing compositions are known in the art.

The composition of the invention comprises a polyol, the reaction product of an antiperspirant salt and a silane and an optional gelling agent, but no or substantially no water. The invention also relates to the process by which compositions of the invention are prepared.

U.S. Pat. No. 4,154,816 (the equivalent of laid-open Dutch patent application No. 75.12239) discloses a hydrophobic solid transparent gelled antiperspirant composition which comprises a monohydric alcohol, di- and/or trihydric polyols or lower polyglycols, a propylene-ethylene glycol polycondensate, dibenzyl sorbitol, antiperspirant metal compounds and a monoor dialkylol amide of higher fatty acids.

However, the material described in U.S. Pat. No. 4,154,816 yields a composition which is sticky to the touch. U.S. Pat. No. 4,346,079 discloses a transparent antiperspirant stick composition based on the material described in 75.12239, but which further contains an amount of an oleaginous compound to control stickiness. The suggested oleaginous compounds are the esters of alcohols with carboxylic acids, hydrocarbons, branched chain and/or unsaturated fatty alcohols and siloxanes. The siloxanes described for use in U.S. Pat. No.4,346,079 are those which have a viscosity of from 0.01 to 25 centistokes, preferably 0.1 to 10 centistokes, such as polydimethyl siloxanes, polyphenylmethyl siloxanes and cyclic polydimethyl siloxanes.

SUMMARY OF THE INVENTION

The present invention relates to antiperspirant compositions which contain no or substantially no water and are transparent or highly translucent in appearance. The invention also relates to antiperspirant compositions as described which may be gelled by the addition of a gellant material thereby giving the antiperspirant composition a consistency suitable for forming or molding into a stick configuration. Furthermore, the invention also relates to the method of making the antiperspirant composition of the invention.

The antiperspirant composition of the invention comprises:

(a) from 5 to 30 wt. % of the reaction product of:
5 to 15 parts by weight of a conventional antiperspirant salt selected from the group consisting of the hydrated chlorine salts of aluminum, zirconium and zinc, the hydrated bromine salts of aluminum, zirconium and zinc and mixtures thereof and preferably, aluminum chlorhydrate, zirconium chlorhydrate and mixtures thereof; and
1 part by weight of a silane of the general formula:

$$R^1Si(OR^2)_3 \qquad (I)$$

wherein $R^1$ represents a member of the group consisting of alkyl groups of from $C_2$ to $C_5$, and aryl groups of from $C_6$ to $C_{18}$, with a $C_3$ alkyl group being the most preferable form of $R^1$, and $R^2$ represents an alkyl group of from $C_1$ to $C_5$, with $C_1$ to $C_3$ being preferable and $C_1$ being most preferable;

(b) from 60 to 95 wt. % of a polyol having the general formula:

$$R^3(OH)_2 \qquad (ii)$$

wherein $R^3$ represents an alkyl group of from $C_2$ to $C_6$, with propylene glycol being the most preferred polyol; and optionally (c) from 0.1 to 10 wt. % of a gellant for said polyol, such as dibenzylidene sorbitol commercially available from Milliken & Co., New York, N.Y., under the tradename MILLITHIX.

The process by which the composition of the invention is prepared comprises the steps of:

(i) preparing an aqueous antiperspirant salt solution by dissolving a conventional antiperspirant salt selected from the group consisting of the hydrated chlorine salts of aluminum, zirconium and zinc, the hydrated bromine salts of aluminum, zirconium and zinc and mixtures thereof and preferably aluminum chlorhydrate, zirconium chlorhydrate and mixtures thereof in water;

(ii) heating said aqueous antiperspirant salt solution;

(iii) adding to the heated aqueous antiperspirant salt solution a mixture of silane:

$$R^1Si(OR^2)_3 \qquad (i)$$

and polyol:

$$R^3(OH)_2 \qquad (ii) \text{ and;}$$

(iv) heating the silane, polyol and antiperspirant salt solution mixture to drive the hydrolysis product of the silane and water and substantially all of the unreacted water therefrom.

The resulting material is a thickened transparent antiperspirant fluid which may be used as is, and would be highly suitable for use in conjunction with a roll-on applicator, spray applicator or other applicator means for applying a liquid to the human underarm. Optionally, the material may be processed further to thicken the fluid into a gel or gelled-solid consistency, so as to facilitate shaping or otherwise forming the material into a stick configuration. The optional gelling step comprises:

(v) Adding a gelling agent to the material produced by the previous step, in an amount necessary to achieve the desired gel consistency.

If the antiperspirant material is gelled, as in step (v), the material may optionally be formed through conventional shaping, extruding or molding processes into a stick configuration for use as an under-arm stick antiperspirant. Shaping and gelling may even be carried out simultaneously, as in the case of adding the gelling agent while the antiperspirant composition is held in a mold for making antiperspirant sticks. The optional shaping step of the method is as follows:

(vi) Shaping the gelled antiperspirant material by conventional means for use as a stick antiperspirant.

An example of the composition of the invention was prepared as follows:

EXAMPLE 1

25 g of aluminum chlorhydrate were dissolved in 75 g of distilled water. The aqueous aluminum chlorhydrate was then was heated at 70° C. for approximately one hour in a three-neck round-bottom flask, then a mixture of 2.5 g propyltrimethoxysilane and 75.0 g propylene glycol was added thereto.

The contents of the flask were then heated to a temperature of 110° C. for four hours. The vapors released by the heated mixture during this time were drawn off from the flask under vacuum and condensed in a dry-ice condenser tube. By collecting and measuring the output of the water from the condenser tube it was apparent that nearly all of the 75 g of water which made up the aqueous antiperspirant salt solution were driven off through heating. The material remaining in the vessel was a clear, somewhat viscous fluid which was found to be soluble in propylene glycol and apparently insoluble, or at least only slightly soluble in water and insoluble in decamethylcyclopentasiloxane.

EXAMPLE 2

10 ml of the antiperspirant fluid obtained in Example 1 were withdrawn from the flask and mixed with 0.2 g of dibenzylidene sorbitol, (MILLITHIX) to form a loose, highly translucent gel.

EXAMPLE 3

To obtain material suitable for forming in a stick configuration, about 5.0 g of a 10 wt % solution of MILLITHIX in propylene glycol was mixed with 10 ml of the antiperspirant fluid obtained in Example 1. A very firm gelled stick was formed therefrom and the appearance of which was reported as translucent with a white haze.

To test the efficacy of the antiperspirant salt in the stick of EXAMPLE 3, the antiperspirant stick was rubbed on the inventor's left forearm and then the inventor exercised, to produce bodily perspiration. The inventor noted that during exercise the left forearm on which the antiperspirant stick had been applied was free of perspiration, whereas the right forearm appeared to perspire normally, indicating the efficacy of the antiperspirant material of the invention.

What is claimed is:

1. A transparent antiperspirant composition comprising:

(a) from 5 to 30 wt. % of the reaction product of:

5 to 15 parts by weight of an antiperspirant salt selected from the group consisting of the hydrated chlorine salts of aluminum, zirconium and zinc, the hydrated bromine salts of aluminum, zirconium and zinc and mixtures thereof; and 1 part by weight of a silane of the formula:

$$R^1Si(OR^2)_3 \quad (i)$$

wherein $R^1$ represents a member of the group consisting of alkyl groups of from $C_2$ to $C_5$, and aryl groups of from $C_6$ to $C_{18}$, and $R^2$ represents an alkyl group of from $C_1$ to $C_5$;

(b) from 60 to 95 wt. % of a polyol having the formula:

$$R^3(OH)_2 \quad (ii)$$

wherein $R^3$ represents an alkyl group of from $C_2$ to $C_6$.

2. A transparent antiperspirant composition comprising:

(a) from 5 to 30 wt. % of the reaction product of:

5 to 15 parts by weight of an antiperspirant salt selected from the group consisting of the hydrated chlorine salts of aluminum, zirconium and zinc, the hydrated bromine salts of aluminum, zirconium and zinc and mixtures thereof; and 1 part by weight of a silane of the formula:

$$R^1Si(OR^2)_3 \quad (i)$$

wherein $R^1$ represents a member of the group consisting of alkyl groups of from $C_2$ to $C_5$, and aryl groups of from $C_6$ to $C_{18}$, and $R^2$ represents an alkyl group of from $C_1$ to $C_5$;

(b) from 60 to 95 wt. % of a polyol having the formula:

$$R^3(OH)_2 \quad (ii)$$

wherein $R^3$ represents an alkyl group of from $C_2$ to $C_6$; and (c) from 0.1 to 10 wt. % of a gellant for said polyol.

3. A transparent antiperspirant composition as claimed in claim 1, wherein $R^1$ is a $C_3$ alkyl group, and $R^2$ is a $C_1$ to $C_3$ alkyl group.

4. A transparent antiperspirant composition as claimed in claim 2, wherein $R^1$ is a $C_3$ alkyl group, and $R^2$ is a $C_1$ to $C_3$ alkyl group.

5. A transparent antiperspirant composition as claimed in claim 3, wherein $R^2$ represents a $C_1$ alkyl group.

6. A transparent antiperspirant composition as claimed in claim 4, wherein $R^2$ represents a $C_1$ alkyl group.

7. A transparent antiperspirant composition as claimed in claim 2, wherein said gellant for said polyol is dibenzylidene sorbitol.

8. A transparent antiperspirant composition as claimed in claim 1, wherein said antiperspirant salt is selected from the group consisting of aluminum chlorhydrate, zirconium chlorhydrate and mixtures thereof.

9. A transparent antiperspirant composition as claimed in claim 2, wherein said antiperspirant salt is selected from the group consisting of aluminum chlorhydrate, zirconium chlorhydrate and mixtures thereof.

* * * * *